United States Patent
Freed et al.

(10) Patent No.: US 8,010,187 B2
(45) Date of Patent: Aug. 30, 2011

(54) THREE-DIMENSIONAL IMPEDANCE IMAGING DEVICE

(75) Inventors: Katherine Freed, Rutherford, NJ (US); Megan Calderia, Forked River, NJ (US); Rachel Ostroff, Jacksonville, FL (US); Esther Eubanks, Perth Amboy, NJ (US); Rainer Martini, Hoboken, NJ (US); Vikki Hazelwood, Wayne, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 375 days.

(21) Appl. No.: 12/358,625

(22) Filed: Jan. 23, 2009

(65) Prior Publication Data

US 2009/0216148 A1   Aug. 27, 2009

Related U.S. Application Data

(60) Provisional application No. 61/023,561, filed on Jan. 25, 2008.

(51) Int. Cl.
*A61B 5/05* (2006.01)

(52) U.S. Cl. ........ 600/547; 600/300; 600/372; 600/382; 702/152

(58) Field of Classification Search .................. 600/300, 600/372, 382, 384, 425, 547, 587; 606/32; 702/150, 152

See application file for complete search history.

(56) References Cited

U.S. PATENT DOCUMENTS

| | | | |
|---|---|---|---|
| 4,263,920 A | 4/1981 | Tasto et al. | |
| 4,291,708 A | 9/1981 | Frei et al. | |
| 4,486,835 A | 12/1984 | Bai et al. | |
| 4,920,490 A | 4/1990 | Isaacson | |
| 5,544,662 A | 8/1996 | Saulnier et al. | |
| 6,236,886 B1 * | 5/2001 | Cherepenin et al. | 600/547 |
| 6,768,921 B2 | 7/2004 | Organ et al. | |
| 6,993,383 B2 | 1/2006 | Assenheimer | |
| 7,212,852 B2 | 5/2007 | Smith et al. | |
| 7,627,362 B2 * | 12/2009 | Gregory et al. | 600/427 |
| 2002/0138019 A1 * | 9/2002 | Wexler et al. | 600/547 |

OTHER PUBLICATIONS

Bayford, R. H., Bioimpedance Tomography (Electrical Impedance Tomography), The Annual Review of Biomedical Engineering (2006) vol. 8, pp. 63-91.

Levy, Shai et al., Electromagnetic Imedance Tomography(EMIT): A New Method for Impedance Imaging, IEEE Transactions on Medical Imaging (2002) vol. 21, No. 6, pp. 676-687.

Cherepenin, Vladimir A. et. al., Three-Dimensional EIT Imaging of Breast Tissues: System Design and Clinical Testing. IEEE Transactions On Medical Imaging (2002) vol. 21, No. 6, pp. 662-667.

(Continued)

*Primary Examiner* — Jeffrey G Hoekstra
*Assistant Examiner* — Charles Becker
(74) *Attorney, Agent, or Firm* — Greenberg Traurig, LLP

(57) ABSTRACT

In a method of electrical impedance tomography (EIT), a mediating fluid provides electrical contact between the electrodes of an EIT device and the skin of a body part to be examined. The height of the fluid is raised or lowered between impedance measurements, enabling tomographic images of the tissue under examination to be resolved mathematically for subsequent viewing. Tomographic planes are isolated by calculating differences between Cartesian models generated from impedance values measured at the plane of interest and at an adjacent plane.

5 Claims, 10 Drawing Sheets

OTHER PUBLICATIONS

Jossinet, J. et. al., A Hardware Design for Imaging the Electrical Impedance of the Breast, Clinical Physics and Physiological Measurement Suppl. A:(1988) vol. 9, pp. 25-28.

Kerner, Todd E. et al., Electrical Imedance Spectroscopy of the Breast: Clinical Imaging Results in 26 Subjects, IEEE Transactions On Medical Imaging (2002) vol. 21, No. 6, pp. 638-645.

Li, Dun et al., Comparisons of Three Alternative Breast Modalities in a Common Phantom Imaging Experiment, Journal of Medical Physics (2003) vol. 30, pp. 2194-2205.

Osterman, K. S. et. al., Multifrequency Electrical Impedance Imaging: Preliminary In Vivo Experience in Breast, Physiological Measurement (2000) vol. 21, pp. 99-109.

Paulsen, Keith D. et al., Alternative Breast Imaging: Four Model-Based Approaches, New York: Spring Science+Business Media, Inc. (2005) pp. 85-126.

Soni, Nirmal et al., A Novel Calibration Scheme for Electrical Impedance Tomography, Physiological Measurement (2003) vol. 24, pp. 421-435.

* cited by examiner

THREE-DIMENSIONAL IMPEDANCE IMAGING DEVICE

CROSS-REFERENCE TO RELATED APPLICATIONS

This application claims the benefit of U.S. Provisional Patent Application No. 61/023,561, filed on Jan. 25, 2008, which is incorporated herein by reference in its entirety.

FIELD OF THE INVENTION

The present invention relates to devices and methods for imaging, and, more particularly, to a device and method for biological imaging.

BACKGROUND OF THE INVENTION

Breast cancer is the most common cancer among women in America, accounting for 15 percent of all cancer deaths. Survival depends strongly on early diagnosis. The foremost breast cancer screening tool is the x-ray mammography. It is estimated that, each year, over 34 million mammograms are conducted in the United States. X-ray mammography can be used to detect variations in tissue density, and when an abnormality is detected, further tests are employed to detect the exact cause of the anomaly.

X-ray mammography is often insufficient for the early detection of breast cancer. Consistent quality is technically difficult to produce and interpretations are variable and subjective. Dense breast tissue and breast cancer both appear white on a mammogram. Therefore, although conventional screening methods have been proven to reduce mortality in women above age fifty, the efficacy of mammography as a life-saving measure in young women is uncertain.

Especially problematic among young women is the higher rate of false-positive and false-negative results. False positives result in over-diagnosis and over-treatment (e.g., 75 percent of biopsied lesions resulting from suspicious mammogram findings turn out to be benign). Furthermore, the false-negative rate has been determined to be as high as 34 percent, increasing the potential mortality for one third of the screened population.

The conventional mammogram is a series of two x-rays, one in the mediolateral oblique view (i.e., from side) and one in the craniocaudal view (i.e., from above). Each film requires uncomfortable compression of the mammary tissue. The mammogram does not detect cancer directly, but is a measurement of tissue abnormalities. Microcalcifications, architectural distortions, masses, and asymmetrical densities can be imaged using this modality. However, conventional mammography cannot distinguish between tissue types or distinguish between in situ lesions or invasive cancer.

Breast biopsies are currently a vital part of the breast cancer screening and detection process to determine the type of tumor harbored in the breast. Biopsies are also able to identify whether the tissue examined is healthy. When the biopsy proves that the anomalous tissue detected by x-ray mammography is indeed healthy, the mammography is said to have produced a false positive. Studies show that testing costs for false positives may be near one-third of the entire mammography cost per year. It has been stated that nearly 75 percent of all tissue biopsies are deemed benign. While the monetary cost is one consideration, the emotional burden ensuing from false-positive results provided by the mammogram cannot be neglected. Women who experience false positives suffer from impaired emotional states for up to three months, with symptoms including impaired moods and limited daily functions. In addition, fear of breast cancer is instilled in most patients receiving false-positive results.

On the other hand, the fact that x-ray mammography machines have sensitivity ratings between 83 and 95 percent leaves them open to missing cancerous growths in the breast tissue. In addition, radiologists' interpretations are not 100 percent accurate and can miss lesions that appear on the film. Poor film quality caused by inadequate x-ray mammographic techniques can also lead to false negatives. Delay in treatment and uncontrolled progression of the disease are possible outcomes of false negatives. In fact, the leading cause of action in medical malpractice lawsuits arises from late or missed breast cancer diagnoses.

Electro-impedance tomography (EIT) is a safe and effective tool for imaging breast tissue regardless of density. The electrical properties of tissue have interested scientists for over 200 years, and researchers have been studying the electrical properties of breast tumors from as early as 1926. The consensus is that malignant breast tumors differ from normal healthy tissue with respect to their electrical properties. Differences in cellular water and electrolyte content, cell membrane permeability, and cell packing reduce the impedance of cancerous tissue. Research in the use of EIT for mammography has resulted in the successful diagnosis of breast cancer in women. Unlike x-ray mammograms, which require a biopsy to differentiate between suspicious tissue types, EIT technology is capable of differentiating among tissue types with less need for biopsies. Furthermore, EIT mammography can create three-dimensional images, which is beyond the capabilities of x-ray mammography. Overall, impedance tomography is more effective, more efficient, and more convenient than x-ray mammography.

EIT mammography is also more economical than x-ray mammography. Impedance-measuring equipment is both compact and inexpensive. The equipment uses small amounts of electricity to run, costing less per image generated. The images are generated on a computer screen and the clinician may print the important images during the examination. Expensive films are unnecessary since tissue images can be printed on less-expensive, high-quality paper or stored and analyzed in pure digital format. In addition, impedance mammography can identify tissue types, reducing the need for biopsy of suspect tissue regions. These factors culminate in a product that is inexpensive to manufacture, inexpensive to operate, and cost-effective.

There are several challenges to creating an effective EIT system. Many current two-dimensional systems create an image of impedance parameters in a single coronal plane (e.g., a view from the front). However, two-dimensional imaging is insufficient to yield clinically accurate results. For example, during impedance scanning of a three-dimensional cylinder, current will naturally traverse out of the two-dimensional imaging plane, extending approximately half of the radius above and below the plane. The presence of heterogeneous tissue above or below the imaging plane will affect the reconstructed images. Three-dimensional EIT is necessary to achieve an accurate reconstruction of the results.

Several research teams have made effective and efficient three-dimensional EIT systems. One obstacle to be overcome is the integration of a three-dimensional electrode array with imaging software. Geometry and size of the tissue to be imaged are two important parameters that must be considered for creation of an accurate image. Both parameters are variable among women. A static geometric electrode array is necessary for comparative studies and clinical use.

Previous applications of EIT have relied heavily on the quality of the contacts between the electrodes and the skin. Errors in placing the electrodes, which cannot be avoided even when the electrodes are applied by a skilled technician, can lead to errors in determining the size and location of anomalous tissues. Further, the electrical signals detected at the electrodes can be distorted by reflective and refractive noise at the skin surface that electrode placement gels neglect. Imaging based on data from electrodes contacting the skin requires the development of a software model that approximates the variations in size and shape of the tissue structure being imaged. For example, if an inflated rubber glove were used as the image of a hand, no person's hand could be accurately imaged. Furthermore, the degree of inaccuracy would vary by patient, making variations difficult to correct by means of software. Instead of fitting breast tissue to a static array or adjusting software for each patient, the technology disclosed herein presents an alternate approach to EIT imaging.

SUMMARY OF THE INVENTION

In one embodiment of the invention, a mediating fluid provides electrical contact between the electrodes of an electrical impedance tomography (EIT) device and the skin of a body part to be examined. The height of the fluid is raised or lowered between impedance measurements, enabling tomographic images of the tissue under examination to be resolved mathematically for subsequent viewing. Tomographic planes are isolated by calculating differences between Cartesian models generated from impedance values measured at the plane of interest and at an adjacent plane.

In another embodiment of the device, sets of impedance measurements are made of the body part in the mediating fluid, which provide experimental impedance values, and sets of impedance measurements are made of the mediating fluid alone, which provide reference impedance values. Separate impedance maps are modeled from the experimental and reference impedance values at each of the fluid levels at which impedance measurements were taken. The values of the reference impedance maps are subtracted from those of the experimental impedance maps to obtain the actual measured impedance values for the body part. A tomographic plane is isolated for viewing by adjusting the actual measured values for that plane through subtraction of the actual measured values for an adjacent plane.

BRIEF DESCRIPTION OF THE FIGURES

For a better understanding of the present invention, reference is made to the following detailed description of the exemplary embodiments considered in conjunction with the accompanying drawings, in which.

DETAILED DESCRIPTION OF THE INVENTION

The technology disclosed herein uses an electrically-conductive mediating fluid to provide an electrical contact between the electrodes of an EIT device and the skin of a body part to be examined. In the EIT method discussed herein, the height of the fluid is raised or lowered between impedance measurements, enabling tomographic images of the tissue under examination to be resolved mathematically for subsequent viewing.

Figure 1:
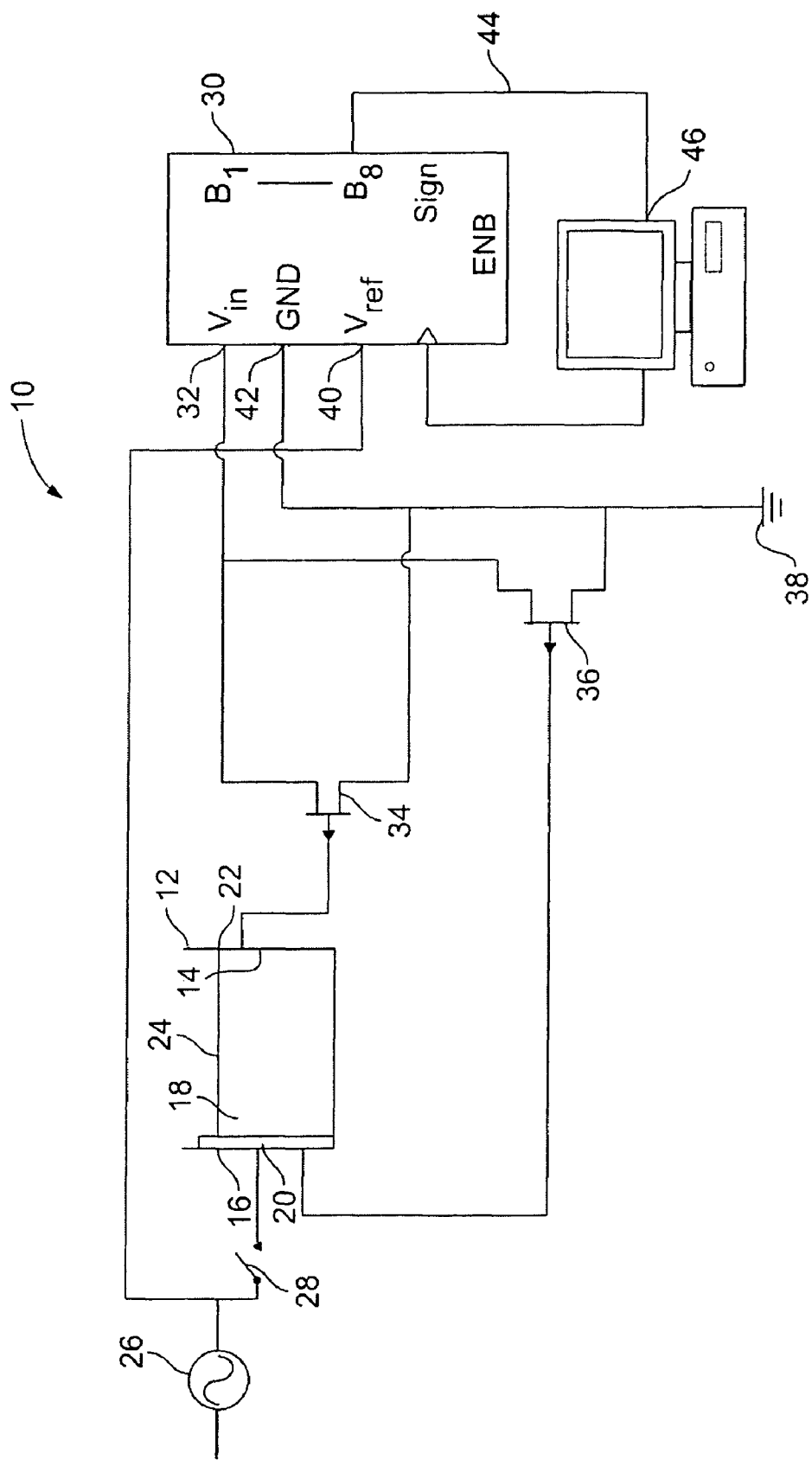
FIG. 1 is a conceptual schematic illustration of an apparatus for EIT imaging according to the present invention.

FIG. 1 illustrates a conceptual example of an apparatus 10 for implementing an EIT method according to the present invention. For the purpose of illustration, the apparatus of FIG. 1 is presented with elements related to three electrodes (not shown). In practice, more than three electrodes should be used, as discussed elsewhere herein. The nature of such electrodes is discussed elsewhere herein.

Referring to FIG. 1, the electrodes are provided as part of testing tank 12 along the inner surface 14 of the tank wall 16. The tank 12 contains an electrically conductive mediating fluid 18 that is in contact with all of the electrodes. The tank 12 is further provided with a fluid level monitor 20 for monitoring the fluid level 22 (i.e., the height of the surface 24 of the mediating fluid 18) within the tank 12. In an embodiment of the apparatus 10, the fluid level monitor 20 is capable of transmitting an electrical signal that varies with the fluid level 22. Fluid sources (not shown) and drains (not shown) would be provided in fluid communication with the tank 12, along with suitable control devices (not shown) to control the fluid level 22 in the tank 12. Suitable types of fluid sources, drains and control devices, as well as their appropriate uses in connection with the present invention, will be known to and understood by those having ordinary skill in the hydraulic engineering field.

Continuing to refer to FIG. 1, a variable-voltage signal generator 26 is electrically connected to one of the electrodes (hereinafter, the "active electrode") through a switching means 28, which can be operated to alternately connect and disconnect the active electrode and signal generator 26. The second and third electrodes are electrically connectable to an analog-to-digital (A/D) converter 30 at its voltage input lead ($V_{in}$) 32, independently of each other, through other switching means 34, 36 which can be operated to alternately shunt an electrical signal detectable at the second or third electrodes to the voltage input lead 32 or to ground 38. Also, the signal generator 26 is electrically connected to the A/D converter 30 at its reference voltage lead ($V_{ref}$) 40. The grounded lead (GND) 42 of the A/D converter 30 is electrically connected to ground 38. A data bus 44 from the A/D converter 30 is connected to a computer 46 which collects the digitized signals from the A/D converter 30, and the signal from the fluid level monitor 20, if present, and executes the software programs for image generation. The computer 46 also executes software programs to coordinate the timing of the switching means 28, 34, 36 with data collection during measurement cycles.

In practice, the tank 12 would be provided with more than three electrodes, each connectible to the signal generator 26 through switching means that perform the same function as switching means 28, and to the voltage input lead 32 and ground 38 through switching means that perform the same functions as switching means 34, 36. The switching functions related to the various electrodes may be coordinated, for example, by software residing in the computer 46, through suitable electrical and mechanical connections. The switching means 28, 34, 36 may be implemented by various devices known in the arts, such as mechanical devices or semiconductor devices, or their functional equivalents. Variations on the electronic scheme of the apparatus illustrated in FIG. 1, such as the transmission of signals from the second and third electrodes to separate A/D converters, and selection of suitable electronic components, as well as the techniques of making connections among the various components of the apparatus 10, will be recognized and understood from the foregoing discussion and the general state of knowledge in the electronic arts.

Tank 12 and its electrodes may have the same configuration as any of the tanks 48, 50, 52, 54, shown in FIGS. 2-9, although other configurations may also be used. The respective electrodes 56, 58, 60, 62 of tanks 48, 50, 52, 54 are fixed in place, thus forming static arrays. The tanks may be constructed of an electrically-insulating material, such as a plastic, and, preferably, one that is medical grade. Polyethylene, polypropylene, polyvinyl chloride (PVC), and polymethylmethacrylate (PMMA, or Plexiglass®) are suitable materials.

Figure 2:
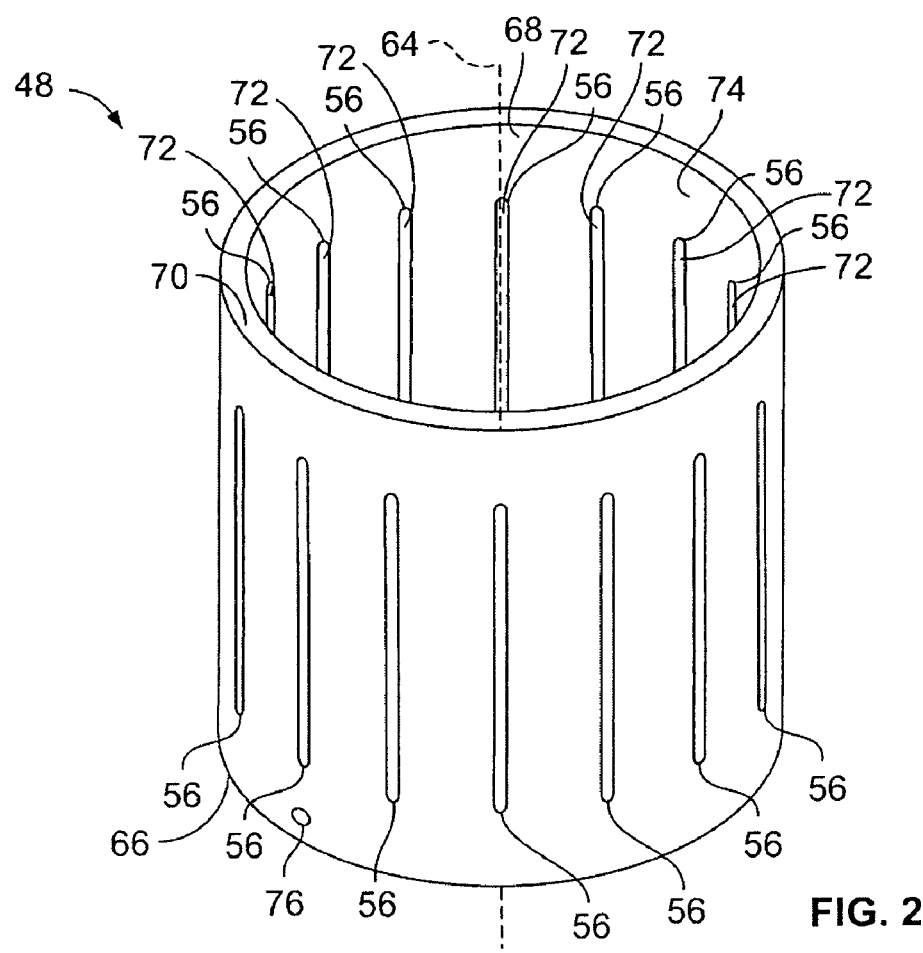
FIG. 2 is a perspective view of a tank equipped with strip electrodes for use in the apparatus of FIG. 1.
Figure 3:
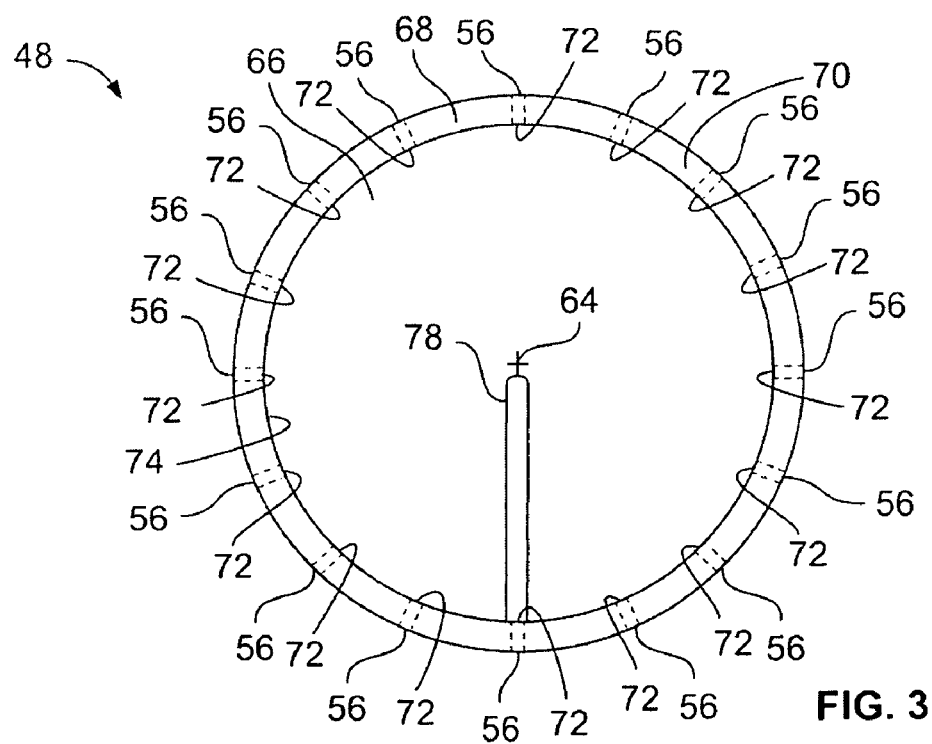
FIG. 3 is a top view of the tank of FIG. 2.

FIGS. 2 and 3 show perspective and top views, respectively, of a cylindrical tank 48 having strip electrodes 56 extending parallel to an axis 64 of the tank 48, between the base 66 and top 68 of the tank 48. In an embodiment of the invention, the electrodes 56 are spaced at equal angles along the tank wall 70, although other spacings may be used in other embodiments. Sixteen electrodes 56 are shown, although other numbers of electrodes may be used in other embodiments. The electrodes 56 have faces 72 exposed at the inner surface 74 of the tank wall 70. In an embodiment of the invention, the electrodes may penetrate the tank wall 70, as shown in FIG. 3. The tank 48 is also provided with a port 76 at its base 66, to provide fluid communication between an inlet pipe 78 and a fluid source (not shown), such as a reservoir, or a drain (not shown), external to the tank 48.

Figure 4:
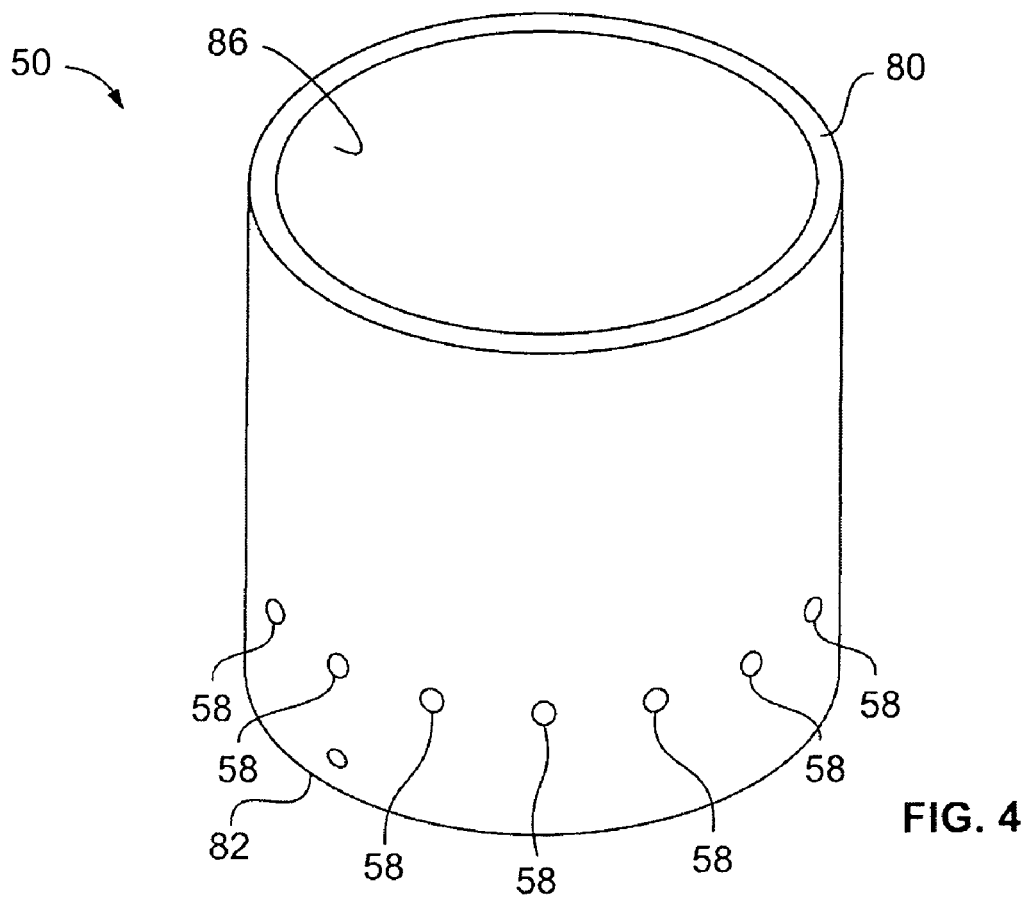
FIG. 4 is a perspective view of the tank of FIG. 2 equipped with point electrodes for use in the apparatus of FIG. 1.
Figure 5:
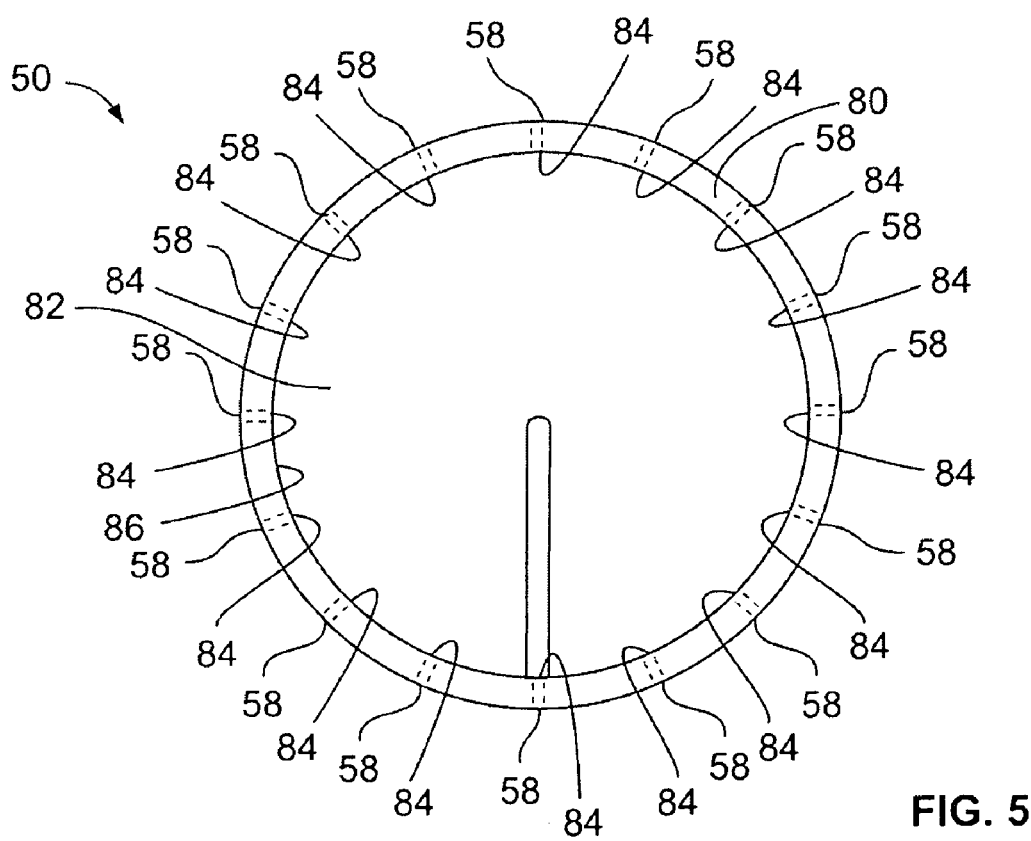
FIG. 5 is a top view of the tank of FIG. 4.

FIGS. 4 and 5 show a cylindrical tank 50 having an array of point electrodes 58 around the circumference of the tank wall 80 near the base 82 of the tank 50, substantially in a single plane. In other embodiments, additional electrodes, similar to electrodes 58, may also be arranged around the tank wall 80, above the electrodes 58. The electrodes 58 have faces 84 exposed at the inner surface 86 of the tank wall 80. In all other respects, the tank 50 is similar to the tank 48 of FIGS. 2 and 3.

Figure 6:
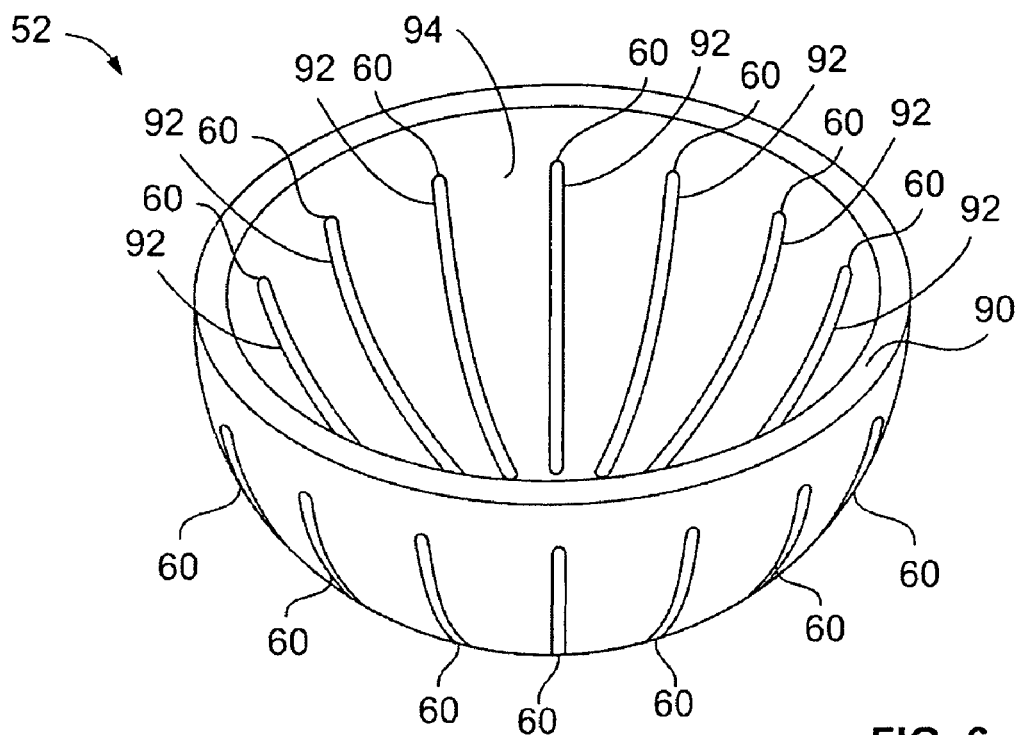
FIG. 6 is a perspective view of another tank equipped with strip electrodes for use in the apparatus of FIG. 1.
Figure 7:
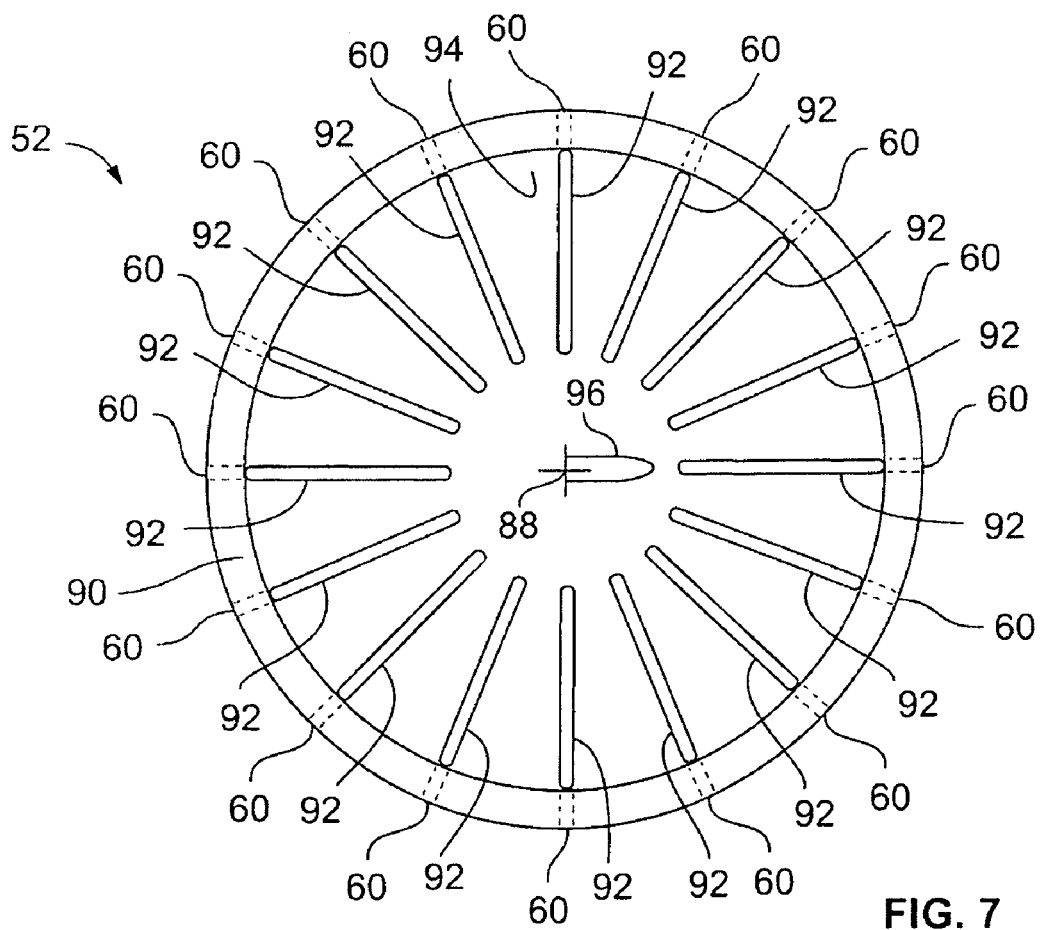
FIG. 7 is a top view of the tank of FIG. 6.

FIGS. 6 and 7 show a semi-spherical tank 52 having strip electrodes 60 radiating from the center 88 of the tank wall 90. The electrodes 60 are spaced at equal angles along the tank wall 90. Sixteen electrodes 60 are shown, although other numbers of electrodes may be used in other embodiments. The electrodes 60 have faces 92 exposed at the inner surface 94 of the tank wall 90. The electrodes 60 may penetrate the tank wall 90, as shown in FIG. 7. The tank 52 is also provided with a port 96 near the center 88 of the tank wall 90 to provide fluid communication between the tank 52 and a fluid source (not shown), such as a reservoir, or a drain (not shown), external to the tank 52.

Figure 8:
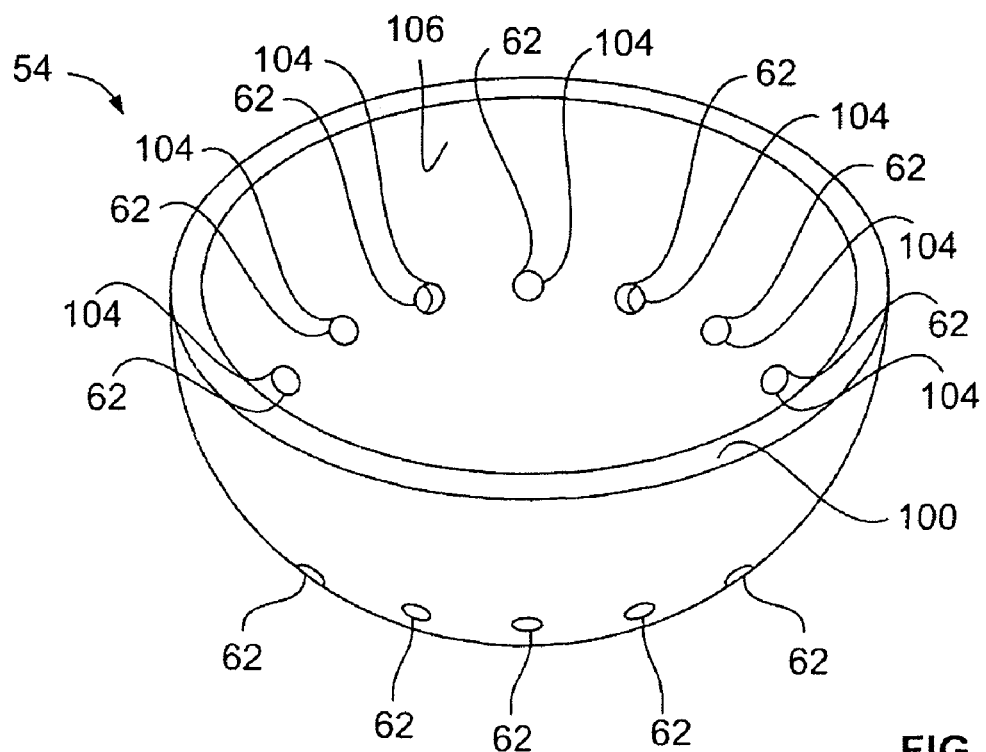
FIG. 8 is a perspective view of the tank of FIG. 6 equipped with point electrodes for use in the apparatus of FIG. 1.
Figure 9:
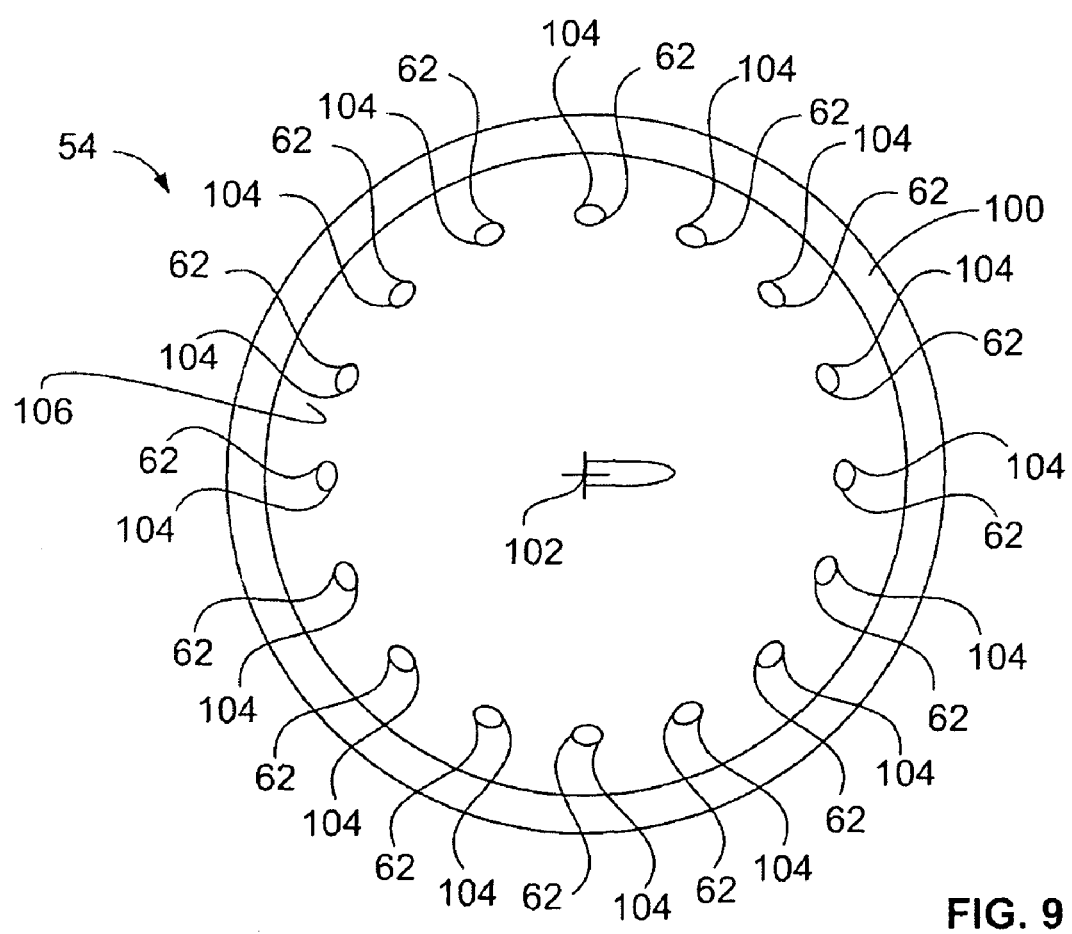
FIG. 9 is a top view of the tank of FIG. 8.

FIGS. 8 and 9 show a semi-spherical tank 54 having an array of point electrodes 62 positioned around the circumference of the tank wall 100 such that the electrodes 62 describe a circle around the center 102. In other embodiments, additional electrodes, similar to electrodes 62, may be arranged so as to describe other circles around the center 102. The electrodes 62 have faces 104 exposed at the inner surface 106 of the tank wall 100. In all other respects, tank 54 is similar to tank 52 of FIGS. 6 and 7.

The cylindrical or semi-spherical shapes of tanks 48, 50, 52, 54 present circular cross-sections through their respective electrode arrays. Such circular cross-sections allow for superior image resolution over cross-sections having other shapes because they minimize the distances between the respective electrodes 56, 58, 60, 62 and create a uniform current density. Further, the circular arrangement of the electrodes 56, 58, 60, 62 simplifies the imaging calculations which are based, in part, on electrode spacing. Tanks having other cross-sectional shapes may be used, as well as those having various arrangements of electrodes, with suitable adjustments to the algorithms used in the imaging calculations.

As discussed above, tanks 48, 50, 52, 54 each have sixteen electrodes 56, 58, 60, 62, respectively. More or fewer electrodes may be used depending, in part, on the image resolution desired, since a more dense electrode array can be used to improve image quality. However, the inclusion of data from larger number of electrodes in the imaging calculations has the potential to increase computation time exponentially.

The electrodes 56, 58, 60, 62 of FIGS. 2-9 are mounted with their respective faces 72, 84, 92, 104 substantially flush with the respective inner surfaces 74, 86, 94, 106 of the tank walls 48, 50, 52, 54 to minimize the formation of tangential signal pathways. The electrodes 56, 58, 60, 62 may have profiles that are flat, triangular, or convex ("lens-shaped"), or have other shapes. The shape and size of the electrodes 56, 58, 60, 62 may be selected to optimize the current density in the mediating fluid 18 (referenced in FIG. 1) for the frequency range and amplitude of a given signal, empirically or through design calculations. Suitable materials for the electrodes will include those that are electrically-conductive, and, preferably, of medical grade. Gold, platinum or 316 stainless steel are suitable electrode materials.

Figure 10:
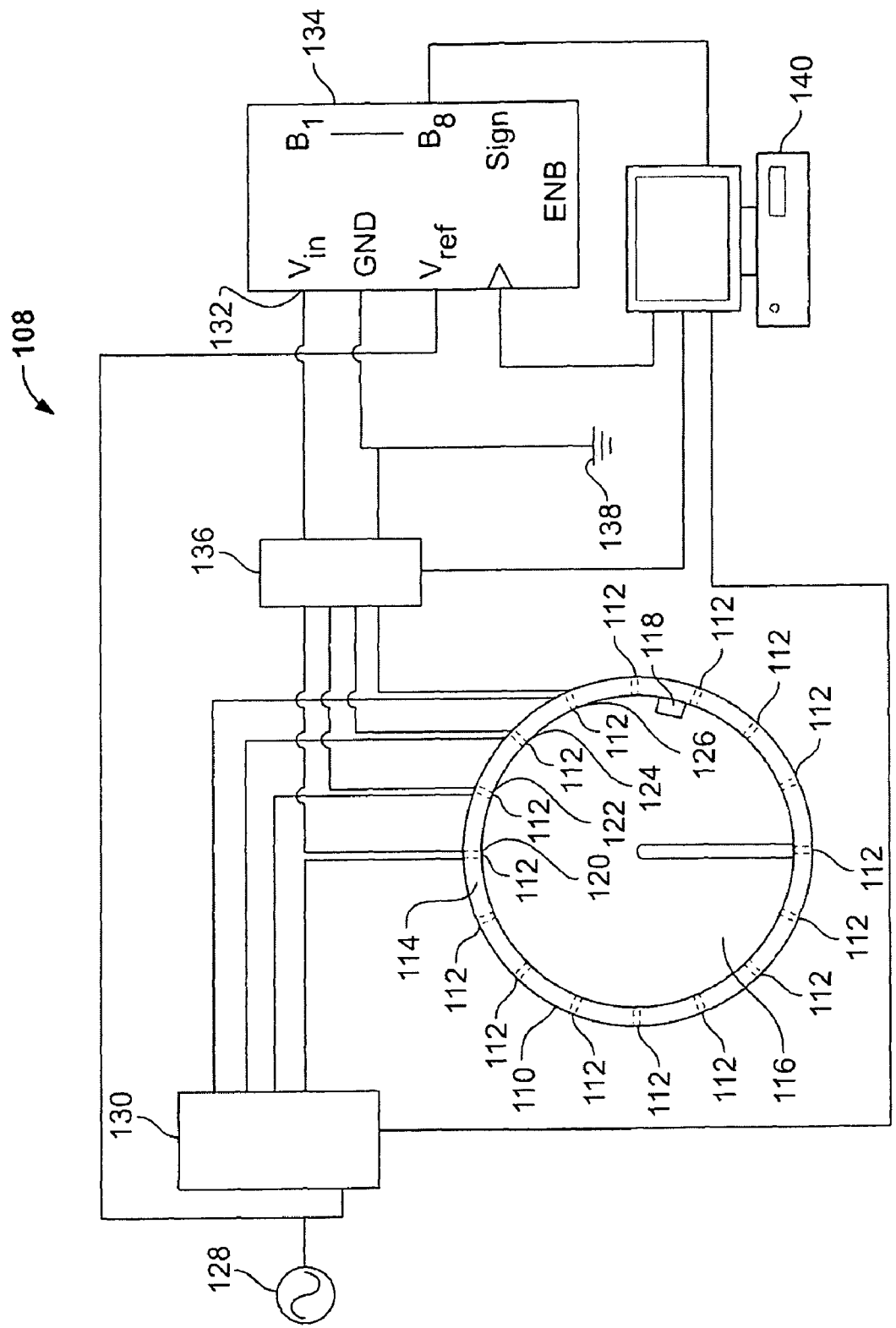
FIG. 10 is a partial schematic of an apparatus for implementation of an EIT method according to the invention.
Figure 11:
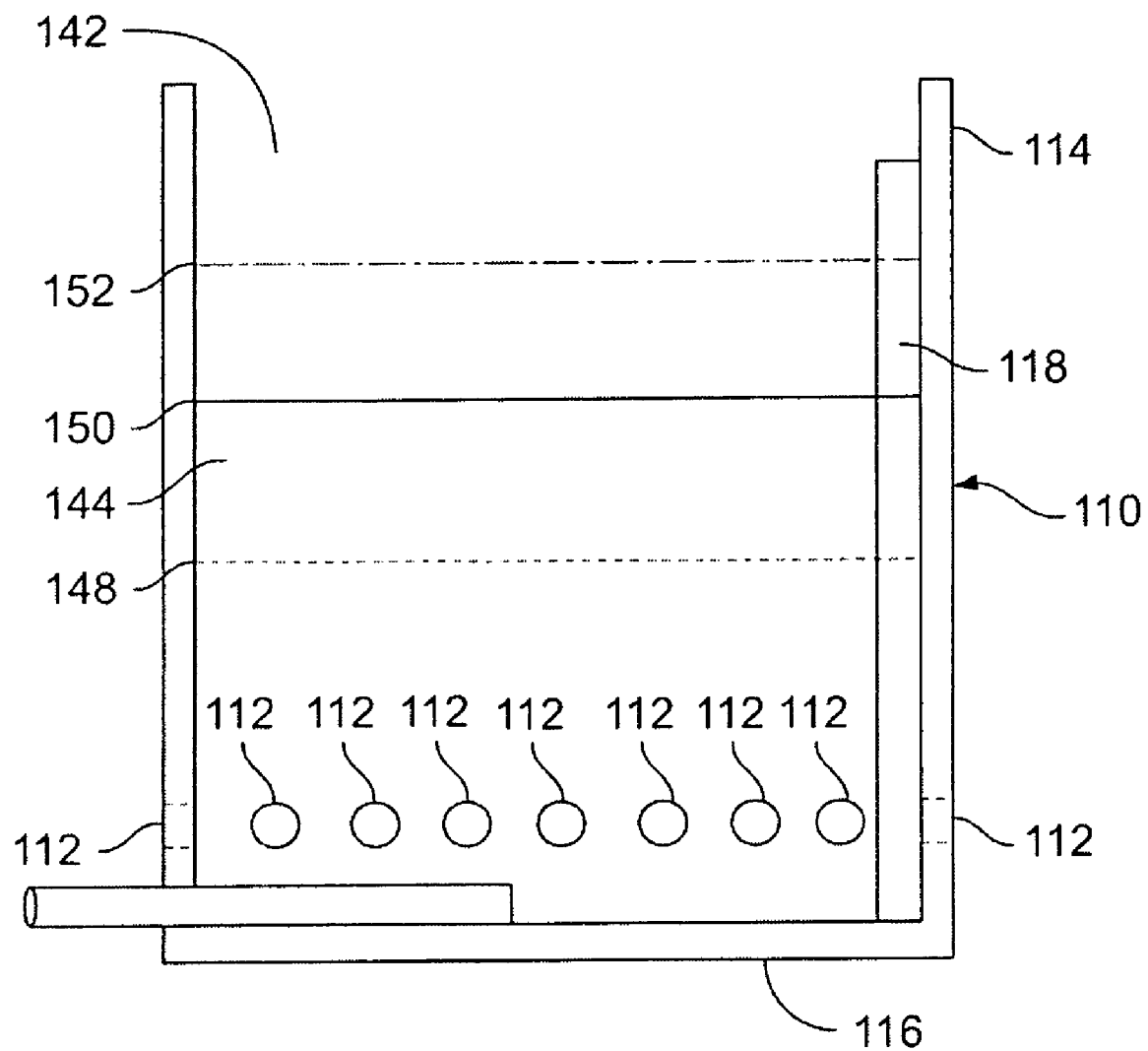
FIG. 11 is a cross-sectional schematic illustration of a portion of an apparatus as used in the calibration process of the implementation of an EIT method according to the invention.
Figure 12:
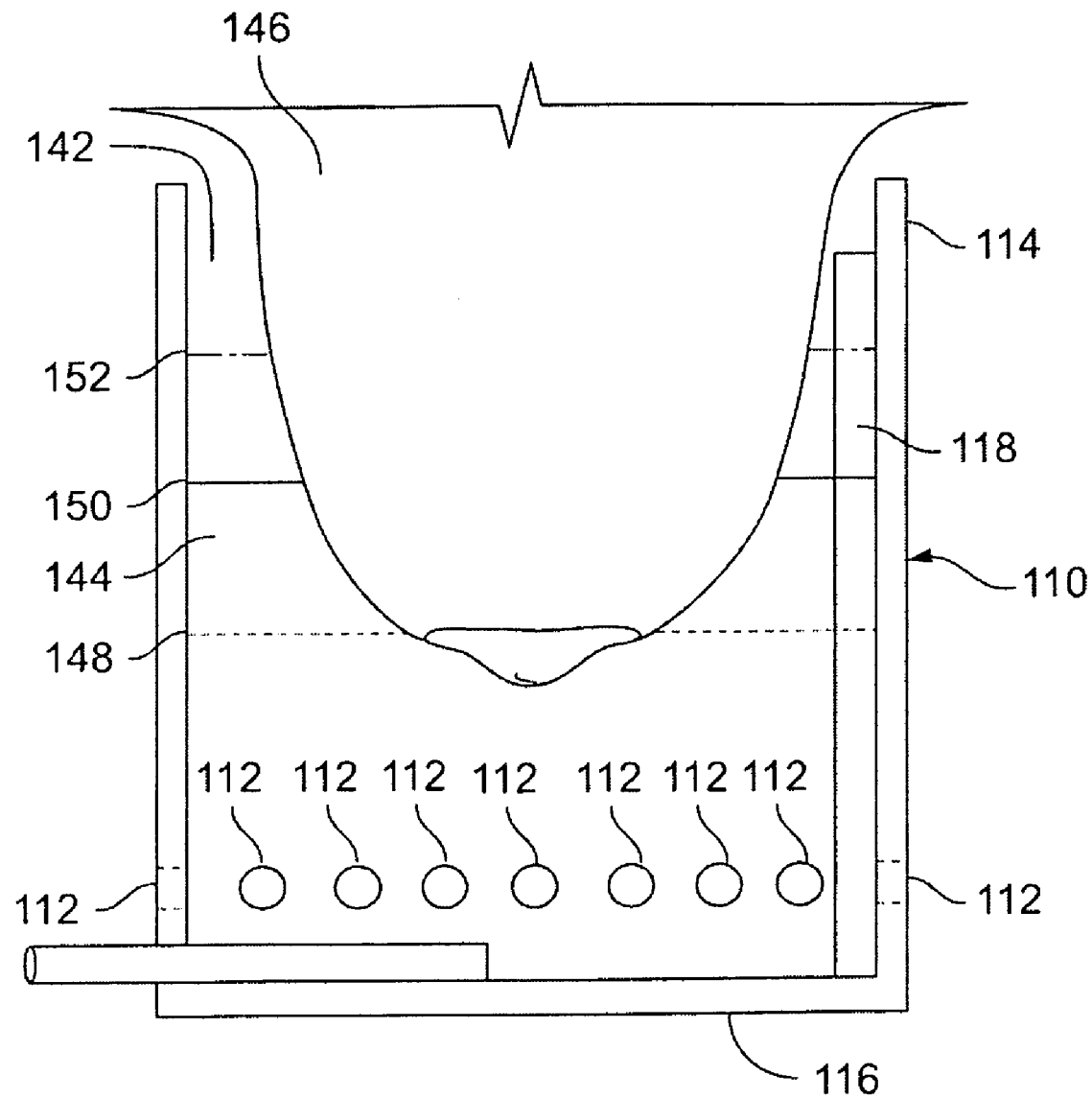
FIG. 12 is cross-sectional schematic illustration of the a portion of an apparatus as used in the examination process of the implementation of FIG. 11.

FIGS. 10-12 are presented to aid in the understanding of an implementation of the EIT method disclosed herein using an apparatus 108 having a cylindrical tank 110 with an array 112 of point electrodes arranged around the tank wall 114 near the base 116 of the tank 110, similar to the arrangement of electrodes 58 of tank 50, illustrated in FIGS. 2 and 3. A fluid level monitor 118 is provided on the tank 110 to monitor fluid levels within the tank 110.

FIG. 10 is a partial schematic of apparatus 108, which is based on a scheme similar to that of apparatus 10 of FIG. 1, and is provided herein to aid in the understanding of a manner in which the measurement steps of the EIT method may be executed. For clarity, the discussion related to FIG. 10 refers specifically to electrodes 120, 122, 124, 126. It will be understood that all of the electrodes in the array 112 are to be operated in the same manner as electrodes 120, 122, 124, 126 and have the same relationships to the other components of the apparatus 108 as do electrodes 120, 122, 124, 126, without those relationships being specifically illustrated or discussed.

Referring to FIG. 10, a variable voltage signal generator 128 is electrically connected to a switching means 130 which can be operated to electrically connect electrodes 120, 122, 124, 126 to the signal generator 130 in a sequence. Electrodes 120, 122, 124, 126 are also connected to the voltage input lead ($V_{in}$) 132 of A/D converter 134 through another switching means 136 which can be operated to shunt signals from the electrodes 120, 122, 124, 126 to ground 138 in another sequence. Hereinafter, the electrode that is electrically connected to the signal generator will be referred to as the "active electrode", the electrode connected to the electrical ground will be referred to as the "grounded electrode", and the other electrodes will be referred to as "passive electrodes". The aforementioned sequences are controlled by computer 140 through the switching means 130, 136 such that, at any time during a measurement cycle, one of the electrodes 120, 122, 124, 126 is the active electrode, another of the electrodes 120, 122, 124, 126 is the grounded electrode, and the remaining ones of the electrodes 120, 122, 124, 126 are passive electrodes. Relationships among the elements of apparatus 108 not specifically referenced or discussed herein will be understood from the description of apparatus 10 of FIG. 1.

A measurement cycle comprises a series of single measurements. In the execution of a single measurement, a sinusoidal signal from the signal generator 128 is driven to the active electrode (e.g., electrode 120). The resulting signals are then measured at the passive electrodes (e.g., electrodes 124, 126, with electrode 122 being the grounded electrode), and converted to digital data as described elsewhere herein. Voltage can be driven to the active electrode and current measured at the active and passive electrodes, or vice versa. After the first measurement has been processed, another single measurement is taken using a different pattern of electrodes (e.g., with electrode 122 as the active electrode, electrode 124 as the grounded electrode, and electrodes 120, 126 as the passive electrodes). Single measurements are then repeated as required by the measurement protocol programmed into the timing software. The driving patterns (i.e., the sequence in which the electrodes 120, 122, 124, 126 are activated or grounded) are not limited in theory, but will be reflected in the computational model implemented by the imaging software. In an embodiment of the invention, the number of single measurements in a measurement cycle is always equal to the number of electrodes in the array 112, with the individual electrodes being driven sequentially (e.g., the signal would first be driven to electrode 120, then to electrode 122, then to electrode 124, and so forth).

In the measurement methodology discussed above, the location of the grounded electrode relative to the active electrode will have an effect on the quality of the image created by the image modeling methodology discussed elsewhere herein. For example, driving patterns in which the grounded electrode is adjacent to the active electrode will provide better image resolution with respect to tissue near the surface of the sample. Driving patterns in which the grounded electrode is opposite the active electrode will provide better image resolution of deeper tissue structures. Measurement cycles could be performed with one electrode permanently grounded, rather than sequentially grounding each of the electrodes. The resolution of the resulting images would be less detailed at the points close to the grounded electrode, and, in extreme cases, would result in a "blind spot" near the grounded electrode.

The frequency of the signal driven to the active electrode is selected such that the impedance calculated from each measurement reflects the electrical properties of the tissue being examined with minimal interference from the mediating fluid. Signal frequencies from about 30 kHz to about 30 MHz have utility in the embodiment of the EIT method discussed herein. A sinusoidal signal frequency of 125 kHz may be used to good effect. In other embodiments of the method, the signal may be driven to the active electrode as a frequency sweep or a pulse sequence allowing a sequential or parallel measurement of multiple frequencies. Safety considerations dictate that predefined thresholds of voltage, current and/or power be observed. For example, in the embodiment of the EIT method discussed herein, the signal applied should not exceed 1 V or 5 mA, for a combined power of 5 mW.

Referring to FIG. 11, in the embodiment of the EIT method discussed herein, the tank 110 is mounted beneath an examination table (not shown) with an opening in the table that allows access to the open top 142 of the tank 110. A mediating fluid 144 is selected to have an impedance similar to the tissue to be imaged (e.g., breast 146 of FIG. 12), and to be biocompatible with that tissue. A buffered saline solution would be a suitable mediating fluid for breast imaging.

Still referring to FIG. 11, mediating fluid 144 is added to the tank 110 to attain fluid level 148 above the electrodes of the array 112. A measurement cycle is executed as discussed above. Mediating fluid 144 is then added to the tank 110 to arrive at fluid level 150, and another measurement cycle is executed. The steps of fluid addition and measurement may be performed as many times as needed (for example, to obtain measurements at fluid level 152) to achieve the desired number of tomographic layers in the imaging process, with the understanding that increasing the number of tomographic layers will proportionately increase the time required to perform the imaging calculations. It may be noted at this point that the measurements obtained by executing the aforementioned steps (i.e., in the absence of the tissue to be examined), will be used as reference data in the imaging computations described elsewhere herein. The steps discussed above will result in a multiple sets of reference data, each set corresponding to a known fluid level 148, 150, 152.

In the embodiment discussed above, fluid levels 148, 150, 152 progress upward from the base 116 of the tank 110 by addition of mediating fluid 114 to the tank 110. In another embodiment, fluid levels 148, 150, 152 may progress in the reverse order by removal of mediating fluid 144 from the tank 110. Changes between fluid levels 148, 150, 152 may be made step-wise or continuously. Measurement cycles may be initiated automatically in response to a signal from fluid level monitor 118 at pre-set fluid levels 148, 150, 152, or manually or automatically while recording the fluid level 148, 150, 152 at which the measurement cycle is initiated. It should be noted that, in either embodiment, each measurement cycle is to be associated with a known fluid level 148, 150, 152 to allow accurate interpretation of the imaging results.

Turning to FIG. 12, after completion of the steps discussed in relation to FIG. 11, the tissue 146 is lowered into the tank 110 from above, and mediating fluid 144 is added or removed to attain fluid level 148. The steps discussed in relation to FIG. 11 are then repeated. Each of the fluid levels 148, 150, 152 to be attained with the tissue 146 present in the tank 110 are the same fluid levels 148, 150, 152 that were attained during execution of the steps discussed with respect to FIG. 11. The identity of the fluid levels 148, 150, 152 between the two series of measurement cycles will allow correlation between the experimental data collected with the tissue 146 present in the tank 110 and the reference data collected with the tissue 146 absent from the tank 110 during the imaging calculations, and aid subsequent interpretation of the images generated.

Figure 13:
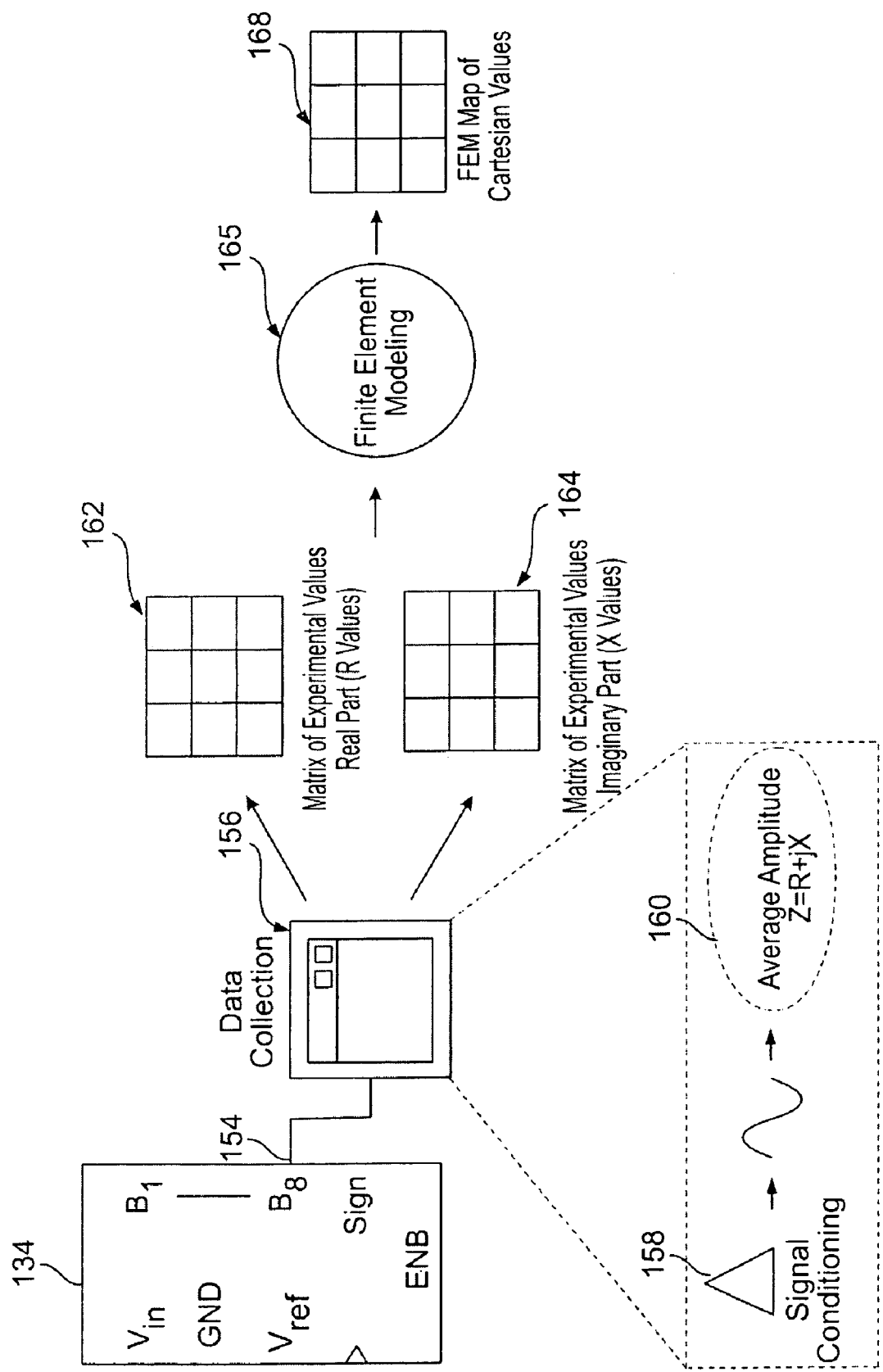
FIG. 13 is a flow sheet of computational steps in an imaging process for implementation in an EIT method according to the invention.
Figure 14:
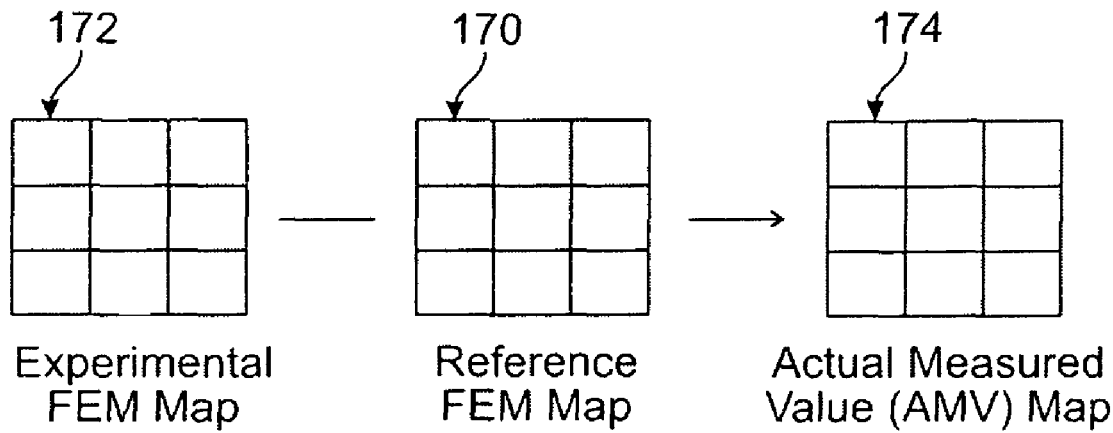
FIG. 14 is a flowsheet of a further computational step in the imaging process of FIG. 13.
Figure 15:
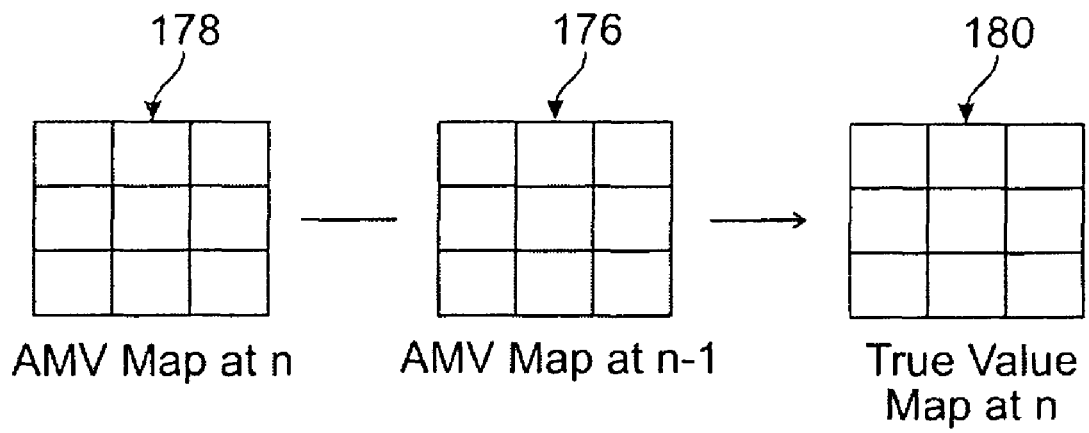
FIG. 15 is a flowsheet of a yet further computational step in the imaging process of FIG. 13.

FIGS. 13-15 are flow sheets of computational steps performed in an imaging process for an embodiment of the EIT method. To facilitate understanding of the imaging computations, the discussion of FIGS. 13-15 may be read with further reference to FIGS. 10-12. To further the understanding of the imaging process, each of the tomographic planes referred to herein is considered to be a planar cross-section taken through the contents of the tank 110 of FIGS. 11 and 12 (i.e. the fluid 144 of FIG. 11 or the fluid 144 and tissue 146 of FIG. 12). The position of any tomographic plane relative to the tank 110 and its contents is the same as that of one of the fluid levels 148, 150, 152 at which a measurement cycle was executed during the steps discussed in relation to FIGS. 11 and 12. Although not shown in any figure, three tomographic planes discussed herein are specifically identified with fluid levels 148, 150, 152, respectively, of FIGS. 11 and 12, and are hereafter referenced as tomographic planes 148', 150', 152' to facilitate discussion of the imaging computations.

Referring to FIG. 13, for a given measurement cycle, whether performed to obtain reference data or experimental data, the signals measured at each electrode are converted from analog form to digital form by the A/D converter 134, which is the same device as A/D converter of FIG. 10. The digital signals, taken, for example, at the digital output lead ($B_8$) 154 of the A/D converter 134, are collected by data collection software 156, conditioned (see element 158) to remove noise (e.g., by using a signal filter such as a bandpass filter), and averaged to obtain an average amplitude. The amplitude data is used to calculate an average impedance value Z (see element 160) by the formula $$Z=V/I=R+jX,$$

where:

V is the voltage applied at the active electrode (or measured at a passive electrode, if a current signal is applied at the active electrode);

I is the current measured at a passive electrode (or applied to the active electrode, if voltage is being measured at the passive electrode);

R is the calculated electrical resistance;

X is the calculated reactance; and j is the imaginary unit.

The resistance value (R) and the reactance value (X) are stored separately in respective matrices 162, 164 for use in subsequent imaging calculations. Each set of matrices 162, 164 is associated with one tomographic plane, such as tomographic planes 148', 150', 152'.

It may be noted at this point that the respective matrices 162, 164 for all measurement cycles should have the same data structure to create correspondence of elements with respect to the different tomographic layers. In one embodiment, the matrices are structured such that each row of each matrix represents values calculated for each single measurement and each column of the matrix represents the values measured at a given electrode during a measurement cycle.

It may be also noted that, in the discussion of FIGS. 13-15 which follows, the imaging calculations are discussed as if performed on one set of values (i.e., on resistance values or reactance values). However, in an embodiment of the invention, the calculations may be carried out on the resistance and reactance values in separate, but parallel, steps.

Referring again to FIG. 13, the values in the matrix 162, 164, for example, those corresponding to tomographic plane 148', are processed by modeling algorithms 166 to construct a numerical image of tomographic plane 148' as a map 168 of calculated values assigned to nodes of a Cartesian mesh. Finite element modeling (FEM) is a well-known method of reconstructing such images from impedance tomography data (see, for example, Paulsen, Keith, D., Paul M. Meaney, and Larry C. Gilman. Alternative Breast Imaging: Four Model-based Approaches. New York: Springer. 2005. pp. 85-126, which pages are incorporated by reference herein in their entirety). The FEM model selected should be tailored for imaging of impedance data, and be capable of performing nodal analysis, although alternative computational methods may be employed. It is beneficial to apply FEM for forward calculations in the modeling process and a regularized non-linear solver for obtaining a unique and stable inverse solution. The applicable computational methods will be well-understood by persons knowledgeable in the data imaging arts.

In the embodiment of the EIT method discussed herein, the calculations discussed in relation to FIG. 13 are performed using the matrix 162 of the real part of the experimental values to create the map 168 (hereinafter, the "FEM map") through FEM. In other embodiments, the matrix 164 of imaginary values could be used, or values from both matrices 162, 164 could be used together, depending on the computational model selected.

Referring now to FIG. 14, using tomographic plane 148' as an example, a reference FEM map 170 has been calculated from the reference data obtained as described in the discussion of FIG. 11 and an experimental FEM map 172 has been calculated from the experimental data obtained as described in the discussion of FIG. 12. Corresponding pairs of maps, similar to maps 170, 172, would also be calculated for each of the other tomographic planes, such as tomographic planes 150', 152'. The maps 170, 172, as well as other maps discussed elsewhere herein, should have the same nodal arrangement, as may be defined by Cartesian coordinates, to create correspondence between the maps generated at each computational step for all of the tomographic planes.

Continuing to refer to FIG. 14, the values in the reference FEM map 170 are subtracted from the values in the experimental FEM map 172 to obtain a map 174 of the actual measured values of tissue impedance (hereinafter, an "AMV map"). This step of the calculations accounts for the effects of the mediating fluid 144 of FIGS. 11 and 12 on the experimental values measured in the respective tomographic plane.

The AMV maps generated for the various tomographic planes do not reflect the true impedance values for the tissue at such planes because of contributions to the signal arriving at the electrodes from outside of the tomographic plane (e.g., the signals measured for tomographic plane 150' would include contributions from the adjacent tomographic plane 148'). Such contributions could be considered to be signal noise. Such signal noise must be accounted for to obtain "true values" for the impedance of the tissue at each tomographic plane, as will be discussed in relation to FIG. 15.

Referring now to FIG. 15, AMV maps 176, 178 have been calculated for tomographic planes 148, 150, respectively. As has been discussed elsewhere, tomographic plane 148' corresponds to fluid level 148 in FIGS. 11 and 12, tomographic plane 150' corresponds to fluid level 150, and tomographic plane 152' corresponds to fluid level 152 in the same figures. Thus, tomographic plane 148' is adjacent to tomographic plane 150', and tomographic plan 150' is adjacent to tomographic plane 152'. In a generalized example, any given tomographic plane could be referred to as "plane n" and the adjacent plane below plane n as "plane n−1". The values of the AMV map at plane n−1 are subtracted from the values of the AMV map at plane n to generate a map of "true values" (hereinafter, a "true value map") for plane n. For the specific example illustrated in FIG. 15, the values in the AMV map 176 of tomographic plane 148 are subtracted from the values in the AMV map 178 of tomographic plane 150 to obtain the true value map 180 of tomographic plane 150. This step would be repeated for successive tomographic planes until true value maps had been generated for each tomographic plane at which measurement cycles had been performed. To continue with the specific example, the values in the AMV map 178 for tomographic plane 152 would be subtracted from the values in the AMV map (not shown) for adjacent tomographic plane 152 to generate a true value matrix (not shown) for tomographic plane 152. The AMV map 176 for tomographic plane 148 would be treated as the true value map for that tomographic plane because the fluid height at fluid level 148 is the smallest in proportion to the radius of tank 110 of FIGS. 11 and 12.

Subsequent to the calculations discussed with respect to FIG. 15, the respective true value matrices may be translated into viewable images using known techniques. Such images may then be viewed in aggregate to approximate a three-dimensional image of the tissue sample. Anomalies in the images, such as those which indicate the presence of a breast tumor, may then be interpreted, according to the clinician's skill, to determine whether further examination or intervention is warranted.

It should be understood that the embodiments described herein are merely exemplary and that a person skilled in the art may make many variations and modifications thereto without departing from the spirit and scope of the present invention. All such variations and modifications, including those discussed above, are intended to be included within the scope of the invention, which is described, in part, in the claims presented below.

What is claimed is:

1. A method of generating a series of tomographic images of a tissue sample, the tissue sample being part of a patient, using an imaging apparatus including a tank having a plurality of electrodes exposed around an interior surface of the tank; an electrically-conductive mediating fluid in the tank in an amount such as to contact the plurality of electrodes; a signal generating means for generating an electrical analog signal; a switching means for electrically and selectively connecting each of the plurality of electrodes individually to the signal generating means such that the electrical analog signal may be driven to the each of the plurality of the electrodes; and at least one computer arranged to perform mathematical calculations, said method comprising the steps of:

(a) placing the tissue sample into the tank;
(b) connecting one electrode to electrical ground, the electrode so connected being a grounded electrode;
(c) adjusting the amount of mediating fluid in the tank to attain a fluid level;
(d) connecting the signal generating means to an electrode that is not the grounded electrode by means of the switching means, the electrode so connected being an active electrode;
(e) driving the analog signal to the active electrode while monitoring one or both of voltage and current at each of the plurality of electrodes so as to obtain measured values of the one or both of voltage and current at each of the plurality of electrodes;
(f) calculating an impedance value associated with the each of the plurality of electrodes from the measured values of one or both of voltage and current;
(g) repeating said steps (d) through (f) for a number of iterations such that no one electrode of the plurality of electrodes is connected to the signal generating means during more than one of the iterations and so as to generate a set of impedance values that includes the impedance values of said step (f), and associating the fluid level with the set of impedance values;
(h) repeating said steps (c) through (g) for another number of iterations so as to create a group of unique fluid levels and a group of sets of impedance values, each of the sets of impedance values being associated with one of the unique fluid levels, the unique fluid levels being identifiable in an order from greater to smaller;
(i) for each of the unique fluid levels, calculating an impedance map of modeled impedance values from the set of impedance values associated with the each of the unique fluid levels and associate the impedance map with the each of the unique fluid levels, the modeled impedance values being calculated by a numerical modeling algorithm and each of the modeled impedance values being mapped uniquely to a node of a Cartesian mesh, the Cartesian mesh being common to all impedance maps so calculated; and
(j) for each of the unique fluid levels except the smallest unique fluid level, calculate an impedance image map by performing a matrix subtraction of the impedance map associated with the next smaller of the unique fluid levels from the impedance map associated with the each of the unique fluid levels and associate the impedance image map with the each of the unique fluid levels, wherein said steps (f), (i) and (j) are performed by means including the at least one computer.

2. The method of claim 1, wherein the set of impedance values of said steps (f) through (i) is a set of experimental impedance values, the modeled impedance values of said step (i) are modeled experimental impedance values, and the impedance map of said step (i) is an experimental impedance map, the imaging apparatus further including another switching means for electrically and selectively connecting each of the plurality of electrodes individually to the electrical ground, said method comprising the further steps of:

(k) adjusting the amount of mediating fluid in the tank to attain a fluid level;
(l) connecting an electrode to electrical ground by means of the another switching means, the electrode so connected being a grounded electrode;
(m) connecting the signal generating means to an electrode that is not the grounded electrode by means of the switching means, the electrode so connected being an active electrode;
(n) driving the analog signal to the active electrode while monitoring one or both of voltage and current at each of the plurality of electrodes so as to obtain measured values of the one or both of voltage and current at each of the plurality of electrodes;
(o) calculating an impedance value associated with the each of the plurality of electrodes from the measured values of one or both of voltage and current;
(p) repeating said steps (l) through (o) for a number of iterations such that no one electrode of the plurality of electrodes is connected to the signal generating means during more than one of the iterations and so as to create a set of reference impedance values that includes the impedance values of said step (o), and associating the fluid level with the set of reference impedance values;
(q) repeating said steps (k) through (p) for another number of iterations so as to create a group of unique fluid levels and a group of sets of reference impedance values, each of the sets of impedance values being associated with one of the unique fluid levels, the unique fluid levels being identifiable in an order from greater to smaller, the number of unique fluid levels in the group being the same as the number of unique fluid levels in the group of step (h) and each of the unique fluid levels being equal to one unique fluid level in the group of step (h);
(r) for each of the unique fluid levels, calculating a reference impedance map of modeled reference impedance values from the set of reference impedance values associated with the each of the unique fluid levels and associate the reference impedance map with the each of the unique fluid levels, the modeled reference impedance values being calculated by a numerical modeling algorithm and each of the modeled reference impedance values being mapped uniquely to a node of a cartesian mesh, the Cartesian mesh being common to all reference impedance maps so calculated; and (s) for each of the unique fluid levels, calculate an impedance map by performing a matrix subtraction of the reference impedance map associated with the each of the unique fluid levels from the experimental impedance map associated with the each of the unique fluid levels, wherein said steps (k) through (q) are performed before said step (a), said step (r) is performed before said step (s), said step (b) is performed such that the electrode of said step (b) is connected to electrical ground by means of the another switching means, and said step (g) is performed such that said step (b) is executed in each of the iterations, and, further, the numerical modeling algorithm of said step (i) is the same as the numerical modeling algorithm of said step (r), and said steps (o), (r) and (s) are performed by means including the at least one computer.

3. The method of claim 2, wherein the at least one computer is arranged to control the switching means and the another switching means, and the execution of said steps (b), (d), (g), (l), (m) and (p) is controlled by means including the at least one computer.

4. The method of claim 1, wherein the at least one computer is arranged to transform digitized data into visual images and displaying such images in a viewable format, said method including the further steps of transforming each of the impedance image maps of said step (j) into a respective visual image and displaying the respective visual image in a viewable format.

5. The method of claim 1, wherein the tissue sample is a breast of a female patient and said method is performed as part of a mammographic examination.

* * * * *

UNITED STATES PATENT AND TRADEMARK OFFICE
CERTIFICATE OF CORRECTION

| | | |
|---|---|---|
| PATENT NO. | : 8,010,187 B2 | Page 1 of 1 |
| APPLICATION NO. | : 12/358625 | |
| DATED | : August 30, 2011 | |
| INVENTOR(S) | : Katherine Freed et al. | |

It is certified that error appears in the above-identified patent and that said Letters Patent is hereby corrected as shown below:

Title Page; item (75); Inventors: Replace "Megan Calderia" with --Megan Caldeira--

Signed and Sealed this
Eighteenth Day of October, 2011

David J. Kappos
*Director of the United States Patent and Trademark Office*